(12) United States Patent
Henke-Sarmento et al.

(10) Patent No.: US 8,196,586 B2
(45) Date of Patent: *Jun. 12, 2012

(54) MEDICAL PROCEDURE DRAPING SYSTEMS

(75) Inventors: Cynthia Ruth Henke-Sarmento, Lakewood, CO (US); B. Hudson Jones, Boulder, CO (US)

(73) Assignee: QSUM Biopsy Disposables LLC, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/845,526

(22) Filed: Jul. 28, 2010

(65) Prior Publication Data
US 2010/0326449 A1 Dec. 30, 2010

Related U.S. Application Data

(63) Continuation of application No. 11/774,483, filed on Jul. 6, 2007, now Pat. No. 7,775,213.

(51) Int. Cl.
*A61B 19/08* (2006.01)
(52) U.S. Cl. .................................................. 128/852
(58) Field of Classification Search .......... 128/849–852, 128/855, 869
See application file for complete search history.

(56) References Cited

U.S. PATENT DOCUMENTS

| | | | |
|---|---|---|---|
| 4,905,710 A | 3/1990 | Jones | |
| 5,522,403 A | 6/1996 | Bark et al. | |
| 5,704,370 A | 1/1998 | Gawarecki | |
| 5,845,641 A | 12/1998 | Pinney | |
| 5,947,122 A | 9/1999 | McDonald | |
| 6,314,958 B1 * | 11/2001 | Harroll et al. | 128/849 |
| 6,497,233 B1 | 12/2002 | DeAngelis | |
| 6,615,836 B1 | 9/2003 | Griesbach et al. | |
| 7,343,919 B2 | 3/2008 | Czajka | |
| 7,775,213 B2 * | 8/2010 | Henke-Sarmento et al. | 128/852 |
| 2006/0150987 A1 | 7/2006 | Dillon | |
| 2007/0079834 A1 | 4/2007 | Reyes et al. | |
| 2007/0102005 A1 | 5/2007 | Bonutti | |

* cited by examiner

*Primary Examiner* — Patricia Bianco
*Assistant Examiner* — Tarla Patel
(74) *Attorney, Agent, or Firm* — HolzerIPLaw, PC

(57) ABSTRACT

A draping system for use in medical procedures includes a drape portion adapted to cover a surface, such as medical equipment or a patient, and serves as a barrier to fluid and debris during medical procedures. The draping system may have a fastening portion affixed to the drape portion and adapted to secure the drape portion to medical equipment. The drape portion may form a pocket for collecting debris resulting from a medical procedure. The drape portion may have an opening therein spanned by a non-porous, elastic membrane.

29 Claims, 4 Drawing Sheets

MEDICAL PROCEDURE DRAPING SYSTEMS

CROSS-REFERENCE TO RELATED APPLICATIONS

The present application claims the benefit of priority to U.S. Provisional Patent Application No. 60/818,927, entitled "Table Draping Systems" and filed on Jul. 6, 2006, specifically incorporated by reference herein for all that it discloses or teaches. The present application is a continuation of U.S. patent application Ser. No. 11/774,483, entitled "Medical Procedure Draping Systems" and filed on Jul. 6, 2007, specifically incorporated by reference herein for all that it discloses or teaches.

BACKGROUND

Drapes are used to cover and protect tables, personnel, and patients during medical procedures, and to improve setup and clean up efficiency before and after such procedures. For example, surgical tables may be covered with new sterile drapes before a procedure in order to create and maintain a sterile field in the medical procedure room. After the medical procedure, the used drapes may be removed and disposed of, thus expediting clean up of the room, and new drapes may be installed in preparation for the next procedure.

Medical procedure draping systems, however, tend to be patterned after bed sheets, with apertures and other features (e.g., adhesives) to facilitate medical procedures. For example, a sheet or absorbent drape may be laid across a surgical table in preparation for a surgical procedure. The patient is laid on the sheet or drape and then covered by an typically rectangular surgical drape, which may have an aperture through which the surgeon can performed the operation. In some applications, the aperture may be treated with adhesives to fix the drape in position around the incision and/or an antimicrobial agent to reduce microorganisms around the incision.

However, the limited selection of typically rectangular surgical drapes is insufficient in protecting a large assortment of medical equipment, particularly those with unusual shapes or placements, or in working well in certain medical procedures. While some surgical tables have a uniform shape and may be easily draped with a sheet or drape having a rectangular shape, other surgical tables and equipment have unique shapes which are not conducive the rectangular shape. If a rectangular drape is used on such tables, the drape may not provide complete or sufficient coverage for the uniquely shaped table. Furthermore, such rectangular drapes are particularly susceptible to slippage from the table or other medical equipment.

Existing surgical drapes can be difficult to set up on such equipment and can be even more difficult to remove from such equipment, especially when trying to safely constrain any debris resulting from the medical procedure, such as liquids (e.g., blood, saliva, etc.), tissue, bone particles, and/or other materials (e.g., soiled gauze pads). As a further concern, medical equipment may have moving structures that are not easily or safely accommodated by existing drapes, particularly in the presence of the debris.

SUMMARY

Implementations described and claimed herein address the foregoing problems by providing a medical procedure draping system that is customized for particular medical equipment and procedures. In one implementation, a medical procedure draping system includes a pocket portion that is continuous with a drape portion to collect debris during medical procedures. In another implementation, a medical procedure draping system includes fasteners to secure a drape to one or more medical devices, such as a surgical table, an instrument, etc. In yet another implementation, a draping system includes an elastic material adhered to a draping portion, wherein the elastic material spans an aperture in the draping portion to allow for the movement of medical equipment relative to the aperture during medical procedures.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTIONS OF THE DRAWINGS

DETAILED DESCRIPTIONS

Figure 1:
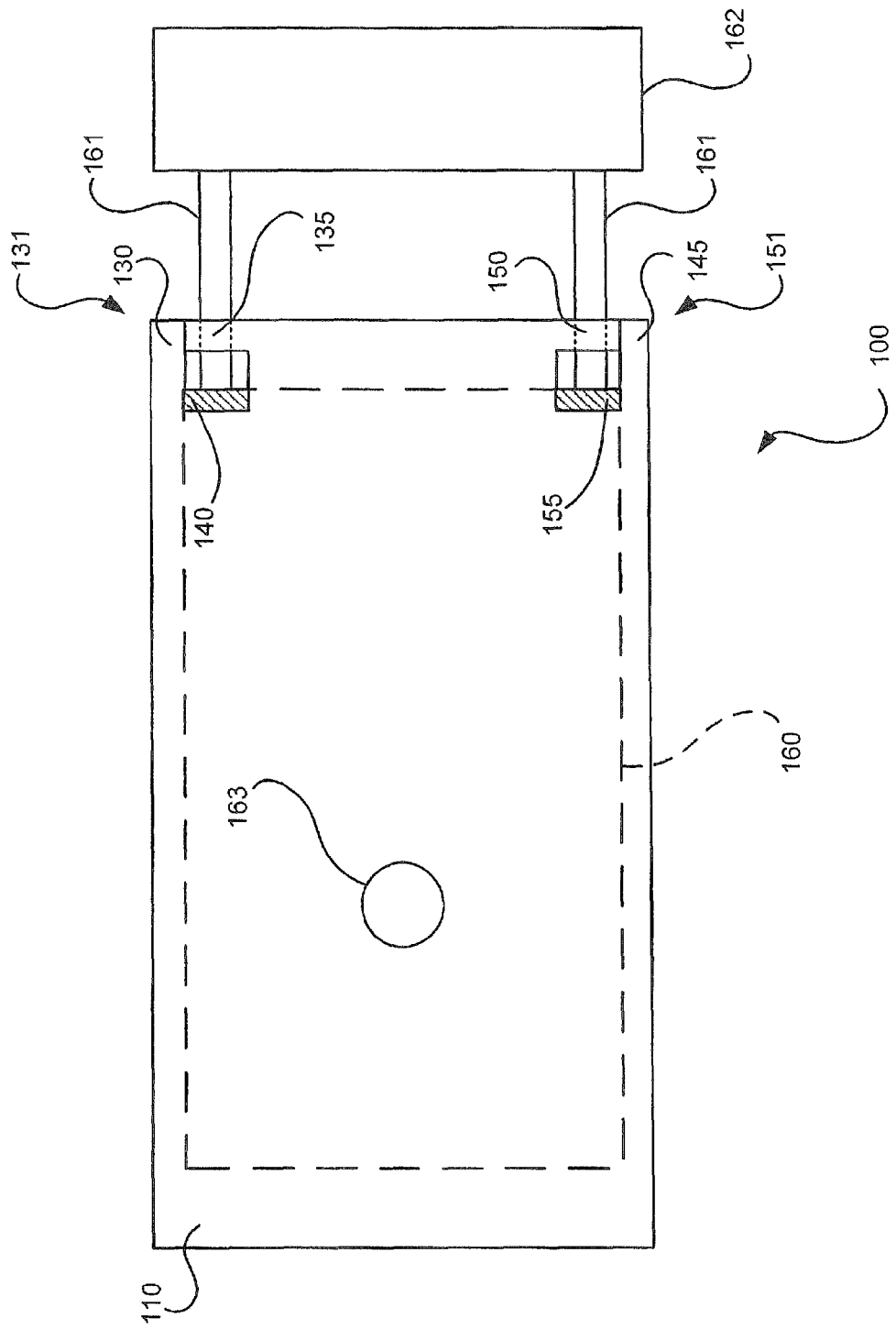
FIG. 1 illustrates an exemplary draping system tabs for securing a drape portion of the draping system to a surgical table.

In one or more implementations of the described technology, a medical procedure draping system is customized to accommodate a set of medical equipment or medical procedures. By incorporating fasteners into a draping system, a drape can be at least partially secured to a piece of medical equipment, substantially reducing movement of the drape during the procedure. The fasteners are positioned within the structure of the draping system to "fit" to the configuration of the medical equipment. For example, fasteners in one implementation of the draping system are positioned at two specific corners of a drape portion in order to engage with shafts extending from the edge of a surgical table having a foot rest supported by the shafts.

In another implementation, the medical procedure draping system forms a pocket for collecting debris resulting from a medical procedure. As such, the draping system does not need to be assembled from multiple components. Instead, a drape of a draping system can be installed as an integrated unit, positioned over the medical equipment such that the debris collects in the pocket during the procedure. Then, the entire drape can be removed as one unit, wrapping around the debris if appropriate, and disposed of. In one implementation, the pocket as well as other portions of the draping system is layered with an absorbent material to further prevent leakage and run-off of such debris.

In yet another implementation, the medical procedure draping system includes an elastic material spanning an aperture in the drape to allow moving medical equipment structures to move against the drape without substantially moving the drape from its position and without tearing the drape material. For example, a needle guide used during a biopsy procedure may move to extend through an aperture in a drape into a biopsy region of a patient. An elastic collar that bounds the aperture and mates snugly with the needle guide provides improved coverage to protect the underlying medical equipment associated with the needle guide from debris (particularly liquid debris) while accommodating the movement of the needle guide without tearing the drape material.

The term "draping system" as used herein includes, but is not limited to, on or more drapes used for a number of different medical procedures, including surgical and/or interventional procedures. Surgical procedures include those procedures performed in an operating room or other surgical environment. Interventional procedures include non-surgical procedures, such as those procedures which do not necessarily need to be performed in an operating room. Interventional procedures include those procedures which are less invasive or less involved, such as those procedures done in a radiology department, including, for example, angiograms, breast biopsies, and lung biopsies. Generally, draping systems described herein may be employed in any medical procedure and/or in association with any medical equipment.

Medical procedure drapes serve several important purposes. They provide a barrier between clinicians/physicians and bodily fluids encountered during medical procedures. Medical procedure drapes protect equipment from fluid invasion that may contaminate the equipment, or cause premature maintenance requirements and/or equipment failure. Further, Medical procedure drapes protect patients from potentially unsanitary conditions left on surgical tables and/or equipment between surgical procedures. Medical procedure drapes may significantly reduce the time required for clean-up between medical procedures, as well as reducing the time required to set-up between medical procedures.

For example, during medical procedures, fluids may be released from the body and run onto or be sprayed onto the drape. Additionally, fluids used during the procedure, such as saline, may run onto or be sprayed onto the drape. Any fluid that is not absorbed by the drape will flow across the surface of the drape, potentially contaminating equipment or coming in contact with the patient or medical staff. Further, the fluids may flow onto the floor, making clean-up more difficult and creating a slippery and potentially hazardous surface.

Prone surgical tables, for example, such as those used in women's healthcare, specifically for performing stereotactic breast biopsy procedures, may require uniquely shaped surgical drapes to ensure proper coverage. A number of different types of prone surgical table systems may be used for performing stereotactic breast biopsy procedures and include, for example, the HOLOGIC LORAD® prone table system and the FISCHER MAMMOTEST® prone table system.

Additionally, surgical tables may be used in conjunction with other medical, equipment that can be covered or accommodated by a drape to protect the equipment debris resulting from the medical procedure. Additionally, such systems may include moving parts that need to remain covered by a drape. Thus, tables that vary in shape and configuration from a standard rectangular surgical table present unique problems in providing adequate coverage with standard rectangular surgical drapes. Likewise, medical equipment used in association with medical procedures can benefit to similar protection.

Drapes may also be used in a number of other industries for a number of different purposes and thus, the description herein is not limited only to drapes for medical and/or surgical purposes. The drapes disclosed herein may be used in non-surgical procedures, on non-prone tables, and also may be used in industries other than health care. For example, drapes may be used to drape tables used in chiropractic and/or massage therapy procedures.

FIG. 1 illustrates an exemplary draping system 100 having tabs 130, 135, 145, and 150 for securing a drape portion 110 of the draping system 100 to a surgical table 160 (shown in dashed outline form below the drape portion 110). In the illustrated implementation, an aperture 163 in the drape portion 110 and the surgical table 160 allow a breast of a patient, who lies prone on the drape portion 110 and the surgical table 160, to be inserted through the aperture 163 to allow for a breast biopsy to be performed using medical equipment positioned underneath the surgical table 160. Accordingly, the drape portion 110 of the draping system 100 provides a barrier between a patient and/or medical personnel (on one side) and the surgical table 160 (on the other side) during medical procedures.

In the implementation shown in FIG. 1, the surgical table 160 includes fixtures 161 (e.g., shafts) that support a foot rest or head rest 162. Accordingly, the draping system 100 incorporates multiple fastening portions 131 and 151. The first fastening portion 131 of the draping system 100 includes tabs 130 and 135, which are affixed or integral to the drape portion 110. To secure the drape portion 110 of the draping system 100 to a corner 140 of the surgical table 160, tabs 130 and 135 of the draping system 100 are wrapped around the nearby fixture 161, brought together, and secured to each other beneath the corner 140 of the surgical table 160. A second fastening portion 151 includes tabs 145 and 150, which are affixed or integral to the drape portion 110. To secure the drape portion 110 of the draping system 100 to a corner 155 of the surgical table 160, tabs 145 and 150 of the draping system 100 are wrapped around the nearby fixture 161, brought together, and secured to each other beneath the corner 140 of the surgical table 160.

The drape portion 110 of the draping system 100 may be formed of any number of different materials such as paper, plastic, cotton, or synthetic materials and may be disposable or reusable. In some implementations, the drape portion 110 may be formed of non-porous materials, for example, spunbond-meltblown-spunbond (SMS) material, spunbond-meltblown-meltblown-spunbond (SMMS) material, or transparent plastic such as clear polyethylene sheeting. Further, a material having a greater absorbency than the drape portion 110 may be affixed to one or more areas of a drape portion to absorb or collect fluids produced during surgical/interventional procedures. The absorbent material may be a pulp-based material, such as AIRLAID®, pulp-based nonwoven material, or any other absorbent material capable of absorbing debris. In yet other implementation, the entire drape portion may be formed of an absorbent material or a combination of absorbent material affixed to a base layer (e.g., plastic, paper, etc.). In still another implementation, the drape portion may be constructed of a combination of absorbent and non-porous materials.

The drape portion 110 may also include a non-slip or non-skid surface to prevent undesired slipping or movement of the drape portion 110 during a surgical/interventional procedure. The drape portion 110 may also contain fragrance or aromatherapy types of products, such as oils or lotions.

One or more fastening portions are affixed or integral to a drape portion of a draping system. In one implementation, a fastening portion includes a pair of independently maneuverable tabs or corner portions affixed to the drape portion. These tabs or corner portions provide adjustable tension in all directions across the surgical table or other medical equipment over which the drape portion is placed. The fastening portion may include a cut-out or slit to create two independently maneuverable portions. The cut-out portion or slit may be a simple slit or cut in the drape portion. In another implementation, a larger opening such as a rectangle, circle, square, or notch may be removed from the drape portion to form a fastening portion. For example, a notch may be removed from the drape portion to accommodate a protruding piece of medical equipment, such as an IV pole. A fastening portion may also be formed by an at least partially perforated slit, which may be torn or divided by a user to more accurately adjust the fit of the drape portion to the medical equipment covered by the drape portion.

The two parts of a fastening portion are secured together using a fastening device. The fastening device may be a two-part device, such as a hook and loop fastener, a hook and eye fastener, a button, a snap, a zipper, ribbons or ties, adhesives, magnets, vinyl adhering fasteners, drawstrings, tabs, hooking devices, sticky glue and other adhesives and belt interlocking devices. Two-part fastening devices are arranged such that one part of the two-part fastening device is positioned on each of the two parts of the fastening portion. Thus, the two parts of the fastening portion can be secured together. Alternatively, fastening devices such as adhesives, self-stick fasteners, and vinyl adhering fasteners may be affixed one of the two parts of the fastening portion to the remaining part of the fastening portion. Thus, one part of the fastening portion can be secured to the remaining part of the fastening portion.

It should also be understood that more than two fastening portions may be employed in a draping system, particularly given the variety of configurations attributed to medical procedure equipment. For example, a surgical table can employ four fixtures that can be used for fastening a draping system to the table, one at each corner. Accordingly, for this configuration, the draping system may employ four fastening portions.

Furthermore, fixtures may take a variety of forms that allow a draping system fastener portion to be fastened thereto, including shafts, rods, snaps, hooks, eyelets, handles, etc. In one implementation, the corner of the table itself may provide a sufficient fixture to which a fastening portion may be secured.

Although FIG. 1 illustrates a draping system that covers a surgical table, it should be understood that the draping system of FIG. 1 may be adapted to cover any type of medical equipment. For example, the draping system may be adapted to cover a footrest or a stage/autoguide of a prone table system. Further, the draping system may be adapted to non-surgical purposes, such as covering an examination table, a massage table used by a physical therapist or a massage therapist, or a table/chair used by a chiropractor.

Figure 2:
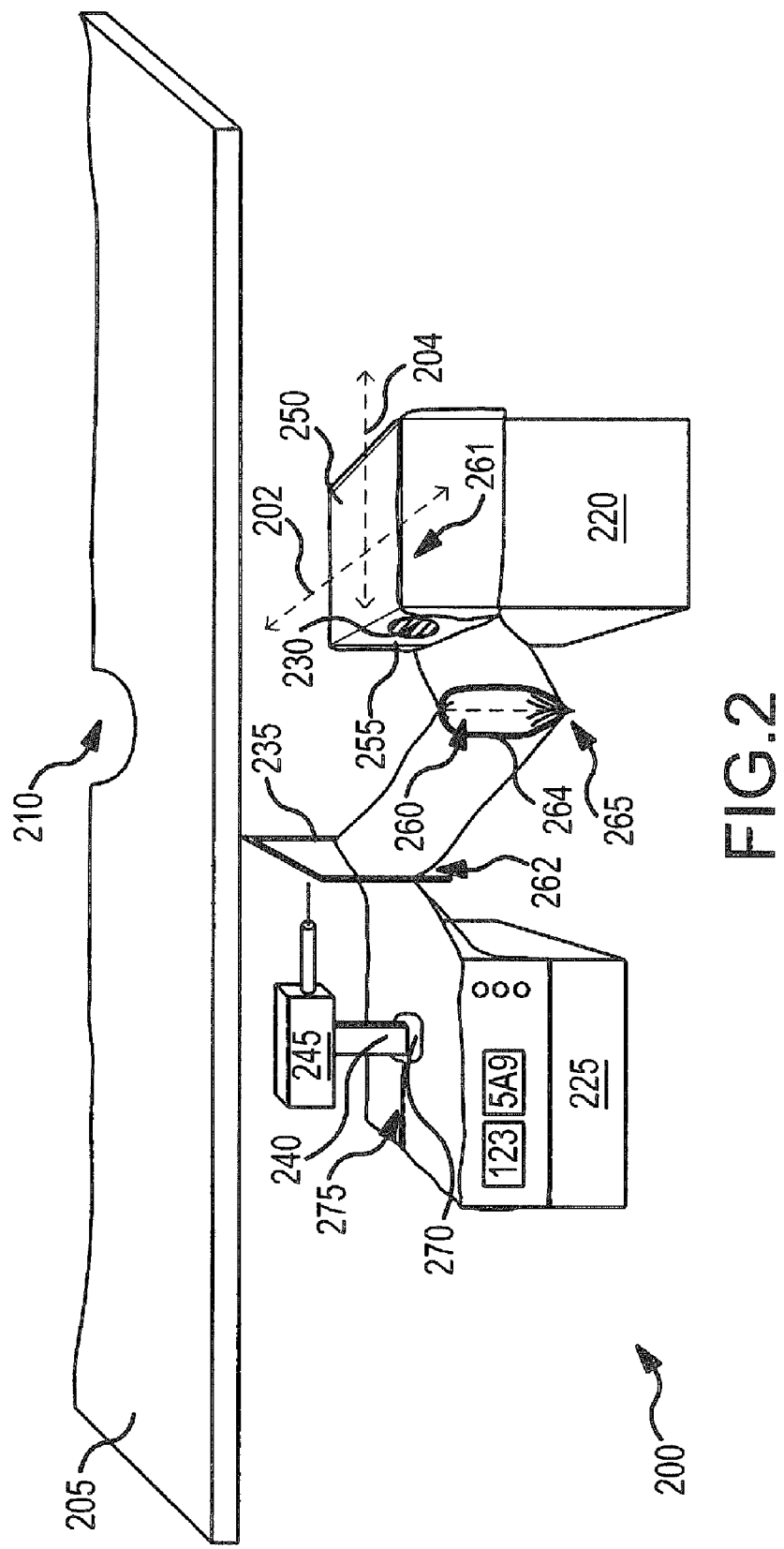
FIG. 2 illustrates an exemplary draping system for covering medical equipment having a drape portion that fauns a pocket for collecting fluid and/or debris resulting from a medical procedure.

FIG. 2 illustrates an exemplary draping system 200 for covering medical equipment 220, 225 having a drape portion 250 that forms a pocket 260 for collecting debris resulting from a medical procedure. In the illustrated implementation, a surgical table 205 having an aperture 210 to allow a breast of a patient, who lies prone on the table, to be inserted through the aperture 210 to allow for a breast biopsy to be performed is positioned above medical equipment 220, 225 for performing the breast biopsy. The drape portion 250 of draping system 200 covers and protects the medical equipment 220, 225 located beneath surgical table 205 from debris that may result from the breast biopsy procedure while allowing a needle guide support 240 and needle guide 245 to extend through the drape 250 so that a breast biopsy procedure may be performed. Accordingly, the drape portion 250 of the draping system 200 provides a barrier between debris (on one side) and medical equipment (on the other side) that may be damaged by debris that may accumulate during medical procedures.

The drape portion 250 illustrated in the implementation shown in FIG. 2 has a transverse axis 202 and a long axis 204. The long axis 204 extends along the length of drape portion 250, from the first piece of medical equipment 220 to the second piece of medical equipment 225. In the implementation shown in FIG. 2, the long axis 204 extends parallel to the length, or the longer of the sides, of surgical table 205. The transverse axis 202 of the drape portion 250 extends along the width of the drape portion 250, orthogonal to the long axis 204. In the implementation shown in FIG. 2, the long axis 204 extends parallel to the width, or the shorter of the sides, of surgical table 205.

As shown in FIG. 2, the drape portion 250 of the draping system 200 covers the first piece of medical equipment 220 that includes an imaging device 230. The drape portion 250 is draped over the medical equipment 220 and may be secured to the underlying medical equipment 220 at a first anchor portion (not shown) on the underside of drape portion 250 using, for example, an adhesive, glue, hook and loop fastener, etc. to prevent the drape portion 250 from moving or shifting under the weight of accumulated debris and exposing the medical equipment 220. Alternatively, the drape portion 250 may be fitted to the shape of the underlying medical equipment to foam an anchor portion.

The drape portion 250 includes a transparent portion 255, such as a transparent polyethylene portion, that allows for the imaging device 230 to capture unobstructed views of the breast inserted that is through aperture 210. The imaging device may be, for example, a gamma camera, which allows for images to be taken of the breast without compressing the breast. In order to image a breast using a gamma camera, a tracing agent is injected into the body of a patient, and the tracing agent is absorbed by all of the patient's cells. The tracing agent concentrates in cancerous cells because cancerous cells have a higher rate of molecular activity. A gamma camera can then be used to determine whether the tracing agent is concentrated in breast tissue by accumulating counts of gamma photons emitted by the tracing agent. Those gamma photons are absorbed by a crystal in the gamma camera, which can then be used to generate an image. In alternative implementations, other radiologic or medical imaging devices may be used.

The drape portion 250 extends along the long axis 204 through a paddle component 235 to cover a second piece of medical equipment 225. In the area of the drape portion 250 that passes through the paddle component 235, the drape portion 250 may include one or more at least partially perforated slits in the transverse direction. The one or more at least partially perforated slits may be opened partially or completely by medical personnel, who can tear or press through any perforations to lengthen the opening, to allow the side portions of the paddle component 235 to extend through the drape portion 250, minimizing bunching or gathering of the drape portion 250 as it passes through the paddle component 235. These partially perforated slits may permit the drape portion 250 to provide greater coverage of any medical equipment or surface located below or adjacent to the paddle component 235. Additionally, these at least partial perforations allow for the drape to be adapted to paddles of different sizes.

In the implementation illustrated in FIG. 2, the paddle component 235 provides support to the drape portion 250 along the transverse axis so that a depression or a pocket 260 is fainted in the drape portion 250 between the first piece of medical equipment 220 and the paddle component 235, and below the paddle component 235. A second anchor portion (not shown) secures the drape portion 250 to the paddle component 235 along the long axis 204 using, for example, an adhesive, hook and loop fastener, snaps, buttons, hook and eye fasteners, ribbons or ties, hooking devices, or other fastening devices. The pocket 260 hangs below the first and second anchor portions of the drape portion 250, forming a depression or valley in the drape portion 250. The second anchor portion minimizes movement of the pocket 260 due to the accumulation of debris in the pocket 260. The paddle component 235, however, is not required to support the drape portion 250. In other implementations, the second piece of medical equipment 225 may provide sufficient support in transverse direction to allow for a depression or pocket to form along the transverse axis between the two pieces of medical equipment or other underlying structures.

In the implementation shown in FIG. 2, a depression in the drape portion 250 forms the pocket 260, which is oriented in the transverse direction between the two pieces of medical equipment 220, 225. Thus, drape portion 250 extends down after passing over the first piece of medical equipment 220, and any debris that falls between the first piece of medical equipment 220 and the pocket 260 will flow across the surface of the drape portion 250 and into pocket 260. The pocket 260 is formed integrally with the drape portion 250. Pleats 265 in the drape portion 250 define the pocket 260 and help to create a well in which debris can collect during a medical procedure. Further, the pleats 265 may increase the capacity of the pocket 260 to hold debris. The pleats 265 may be formed, for example, by folding the drape portion 250 and securing the edges of the fold using, for example, an adhesive, clamp, crimping device, or other method of fixation. The drape portion 250 may be folded, accordion-style, along the transverse axis to form pleats 265. In an implementation, a reusable adhesive or fixative may be used to secure the pleats so that the number of pleats can be adjusted by a medical professional, based on the amount of debris anticipated to result from the medical procedure. The pocket 260 may be formed of or lined with an absorbent material such as AIRLAID , pulp-based nonwoven material, or any other absorbent material capable of absorbing debris. Additionally, a ridge may be formed around the edge of the pocket to reduce or prevent the leakage of debris from the pocket. This ridge may be formed, for example, by a ring of absorbent material affixed to the drape portion to contain any debris that collects or pools in the pocket.

From the pocket 260, the drape portion 250 extends along the long axis and is draped so that the drape portion 250 has an upward slope as it moves away from the pocket 260. This slope allows for gravity to carry any debris that falls on this portion of the drape to flow into and be contained by the pocket 260. The drape portion 250 is fed through the paddle component 235, which serves to compress the breast and provides support to the drape portion 250 along the transverse axis. In an alternative implementation, the second piece of medical equipment 225 or other underlying structure could provide support for the drape portion 250.

Drape portion 250 then extends along the long axis to cover the second piece of medical equipment 225. The section of drape portion 250 that covers the second piece of medical equipment 225 includes a slit 275 to accommodate protruding medical equipment, such as needle guide support 240 that supports a needle guide 245. The slit 275 may be partially perforated to allow for a user to tear or divide the drape portion to accommodate protruding medical equipment. Alternatively, the slit 275 may persist through the thickness of the drape portion 250. Further, an adhesive, clip, or other fastening mechanism may be used to secure the two sides of the slit to each other and/or the underlying medical equipment, in order to prevent debris from coming in contact with the underlying medical equipment. Thus, the two edges of the slit can be brought together and fastened around a protruding piece of medical equipment to prevent debris from contacting medical equipment 225.

Further, as illustrated in FIG. 2, to prevent debris from seeping through the drape portion 250 where the needle guide support 240 protrudes through the drape portion 250 and to allow for movement of the needle guide support 240 and needle guide 245, the portion of slit 275 that surrounds the needle guide support 240 is formed of a nonporous, elastic membrane 270. The nonporous, elastic membrane 270 Rams a boot or collar around the based of the needle guide support 240. Thus, the nonporous, elastic membrane 270 serves a barrier to debris and protects the underlying medical equipment. Additionally, the nonporous, elastic membrane 270 stretches to accommodate movement, such as the movement of the needle guide support 240 and needle guide 245, during a biopsy procedure. Thus, the needle guide support 240 or other medical equipment can move during a medical procedure without tearing or dislodging the drape portion 250.

The drape portion of the draping system may be form of any number of different materials such as paper, plastic, cotton, or synthetic materials and may be disposable or reusable. In some implementations, the drape portion may be formed of non-porous materials, for example, spunbond-meltblown-spunbond (SMS) material, spunbond-meltblown-meltblown-spunbond (SMMS) material, or transparent plastic such as clear polyethylene sheeting. Further, the pocket may be lined with a material having a greater absorbency than the drape portion to absorb or collect fluids/debris produced during surgical/interventional procedures. The absorbent material may be, for example, a pulp-based material such as AIR-LAID®, pulp-based nonwoven material, or any other absorbent material capable of absorbing debris. In yet other implementation, the entire drape portion may be formed of an absorbent material such as AIRLAID®, pulp-based non-woven material, or any other absorbent material capable of absorbing debris. In still another implementation, the drape portion may be constructed of a combination of absorbent and non-porous materials. The drape portion may also include a non-slip or non-skid surface to prevent undesired slipping or movement of the drape portion during a surgical/interventional procedure. The drape portion may also contain fragrance or aromatherapy types of products, such as oils or lotions.

It should also be understood that, while FIG. 2 illustrates an implementation having a pleated pocket, a pocket may be formed in the drape portion without pleating the drape portion. Additionally, it should be understood that more than one pocket can exist within the same drape portion and draping system. For example, in the draping system illustrated by FIG. 2, an additional pocket could be formed in the draping system between the paddle component 235 and the second piece of medical equipment 225, by positioning the drape portion 250 so that it droops and forms a depression or valley between the paddle component 235 and the second piece of medical equipment 225.

In still another implementation, a pocket may be created by pleating the end of the drape portion and positioning the drape such that the pocket is below the rest of the drape portion. Thus, any fluids/debris on the drape runs into the pocket. For example, a patient sitting upright could be covered by such a draping system. The drape portion may be fastened around the patient's upper body with the pocket positioned at the bottom of the drape portion. With the pocket formed at the end of the drape portion, gravity will cause fluid and debris that drip on the drape portion to pool or collect in the pocket. Further, pockets may be created at both ends of a drape portion such that, when a drape is placed over a reclining patient, the patient's body serves as a high point in the drape portion and the two pockets lie on either side of the patient. Thus, gravity causes any fluid/debris to run off into one of the two pockets rather than onto the floor or patient.

Figure 3:
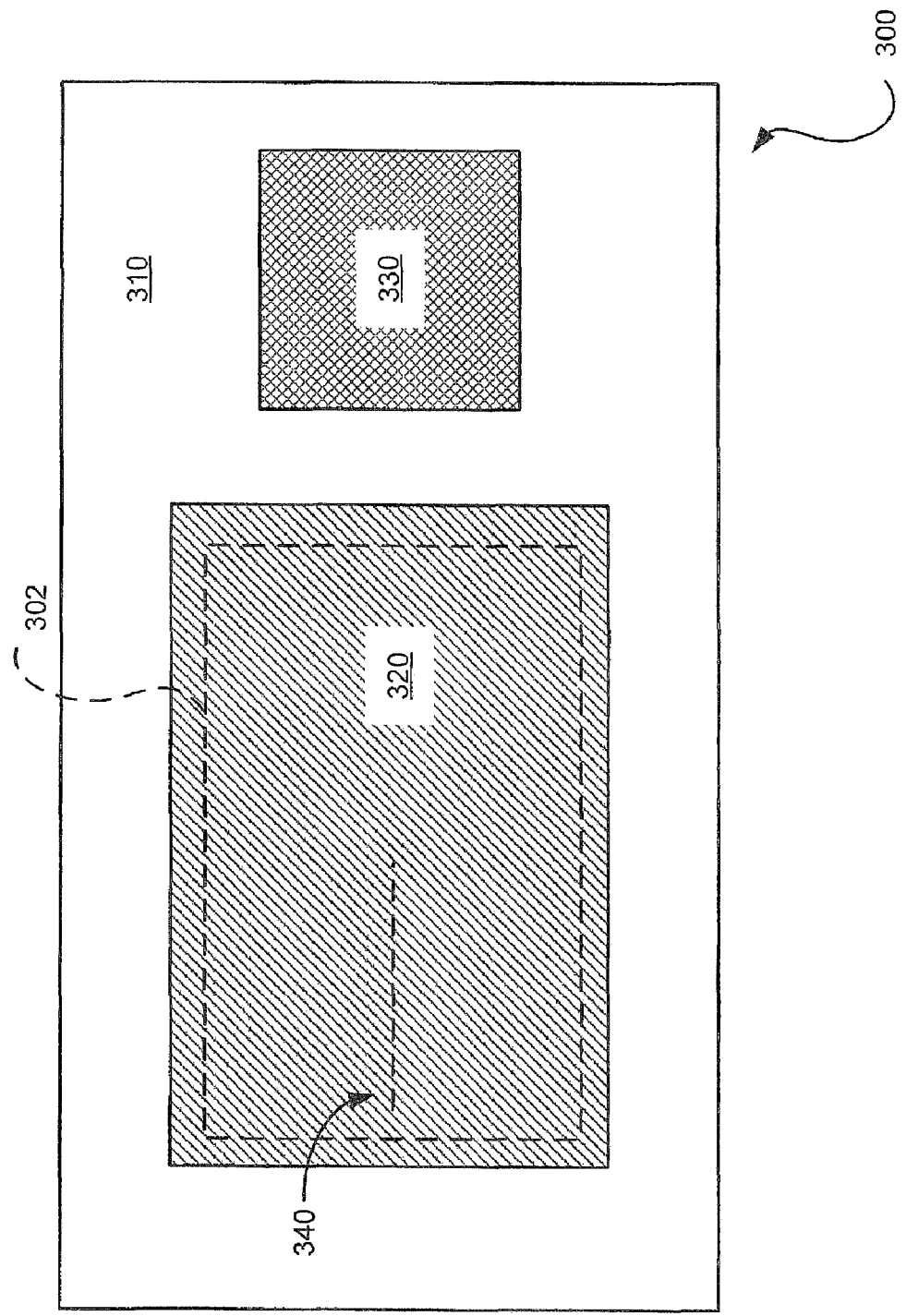
FIG. 3 illustrates an exemplary draping system with a drape portion that has an opening spanned by a nonporous, elastic membrane.

FIG. 3 illustrates an exemplary draping system 300 with a drape portion 310. In the illustrated example, the drape portion 310 is formed of a thin, nonporous transparent plastic sheet, although other materials may be employed. An aperture 302 in the drape portion 310 allows movable or adjustable medical equipment (e.g., a needle guide support, a needle guide, etc.) to be inserted through the drape portion 310 during a medical procedure, such as shown by needle guide support 240 in FIG. 2. The aperture 302 allows the medical equipment to move relative to the drape portion 310 during the procedure without moving the drape portion 310 from the surfaces it is protecting.

Furthermore, by spanning the aperture 302 with a nonporous elastic membrane 320, which also includes an aperture 340, the medical equipment below the aperture 302 may be continue to be well protected from debris resulting from the medical procedure. The aperture 340 may be formed as an at least partially perforated slit 340 in the nonporous, elastic membrane 320. The aperture 340 may also be opened more fully by medical personnel, who can tear or press through any perforations to widen and/or length the opening. The apertures 302 and 340 allow for items such as medical instruments to extend through the drape portion 310 and the nonporous, elastic membrane 320, which can form a boot or collar around the medical equipment. As such, the nonporous, elastic membrane 320 serves as a barrier to debris and protects underlying medical equipment from invasion by debris. Additionally, the nonporous, elastic membrane stretches 320 to accommodate movement, such as the movement of a needle guide during a biopsy procedure, during a medical procedure without tearing or dislodging the drape portion 310.

Additionally, FIG. 3 illustrates an absorbent material 330 affixed to the drape portion 310 to collect and absorb debris. In FIG. 3, the absorbent material 330 is positioned to collect debris that may fall from the needle during the biopsy procedure. The absorbent material may be permanently affixed to the drape portion 310. Alternatively, the absorbent material could be cut to a desired size by a medical professional and affixed an area of the drape portion 310 at any position where debris is likely to accumulate using, for example, an adhesive, double sided tape, a hook and loop fastener, or the like. Further, multiple pieces of absorbent material may be affixed to the drape portion 310, as required by the medical procedure to be performed. For example, if multiple incisions are required, absorbent material may be affixed to the drape portion at locations adjacent to the incision sites.

The drape portion of the draping system, which has an opening therein, may be formed of any number of different materials such as paper; plastic, cotton, or synthetic materials and may be disposable or reusable. In some implementations, the drape portion may be formed of non-porous materials, for example, spunbond-meltblown-spunbond (SMS) material, spunbond-meltblown-meltblown-spunbond (SMMS) material or transparent plastic such as clear polyethylene sheeting. Further, a material having a greater absorbency than the drape portion may be affixed to the drape to absorb or collect fluids/debris produced during surgical/interventional procedures. The absorbent material may be, for example, a pulp-based material such as AIRLAID®, pulp-based nonwoven material, or any other absorbent material capable of absorbing debris. In yet other implementation, the entire drape portion may be formed of an absorbent material such as AIRLAID®, pulp-based nonwoven material, or any other absorbent material capable of absorbing debris. In still another implementation, the drape portion may be constructed of a combination of absorbent and non-porous materials. The drape portion may also include a non-slip or non-skid surface to prevent undesired slipping or movement of the drape portion during a surgical/interventional procedure. The drape portion may also contain fragrance or aromatherapy types of products, such as oils or lotions.

In an implementation, the drape portion includes an at least partially perforated slit, which may be torn or divided by a user to more accurately adjust the fit of the drape portion to the surface covered by the drape portion. Alternatively, the at least partially perforated slit may be torn or divided by a user to accommodate a piece of medical equipment, such as an IV pole. The drape portion may be secured by an adhesive or other fastener.

The non-porous, elastic membrane, that spans the opening in the draping portion may be, for example, an elastomeric or rubber material. The non-porous, elastic membrane may include latex or non-latex materials, such as KRATON® latex. The non-porous, elastic membrane is affixed to the drape portion using, for example, an adhesive suitable for the membrane material and drape material used, such as adhesive tape, hot melt adhesive, or cold glue. The non-porous, elastic membrane may be affixed to the drape portion to allow for stretching of the non-porous elastic membrane without tearing or damaging the draping system.

In an implementation, the non-porous elastic membrane may span an opening in a nonabsorbent, clear polyethylene drape portion. In another implementation, the non-porous elastic membrane may span an opening in a drape portion formed of an absorbent material, such as AIRLAID®, or any other absorbent material capable of absorbing bodily fluids. Additionally, the non-porous elastic membrane may be affixed to an underlying surface using, for example, adhesive or adhesive tabs.

Figure 4:
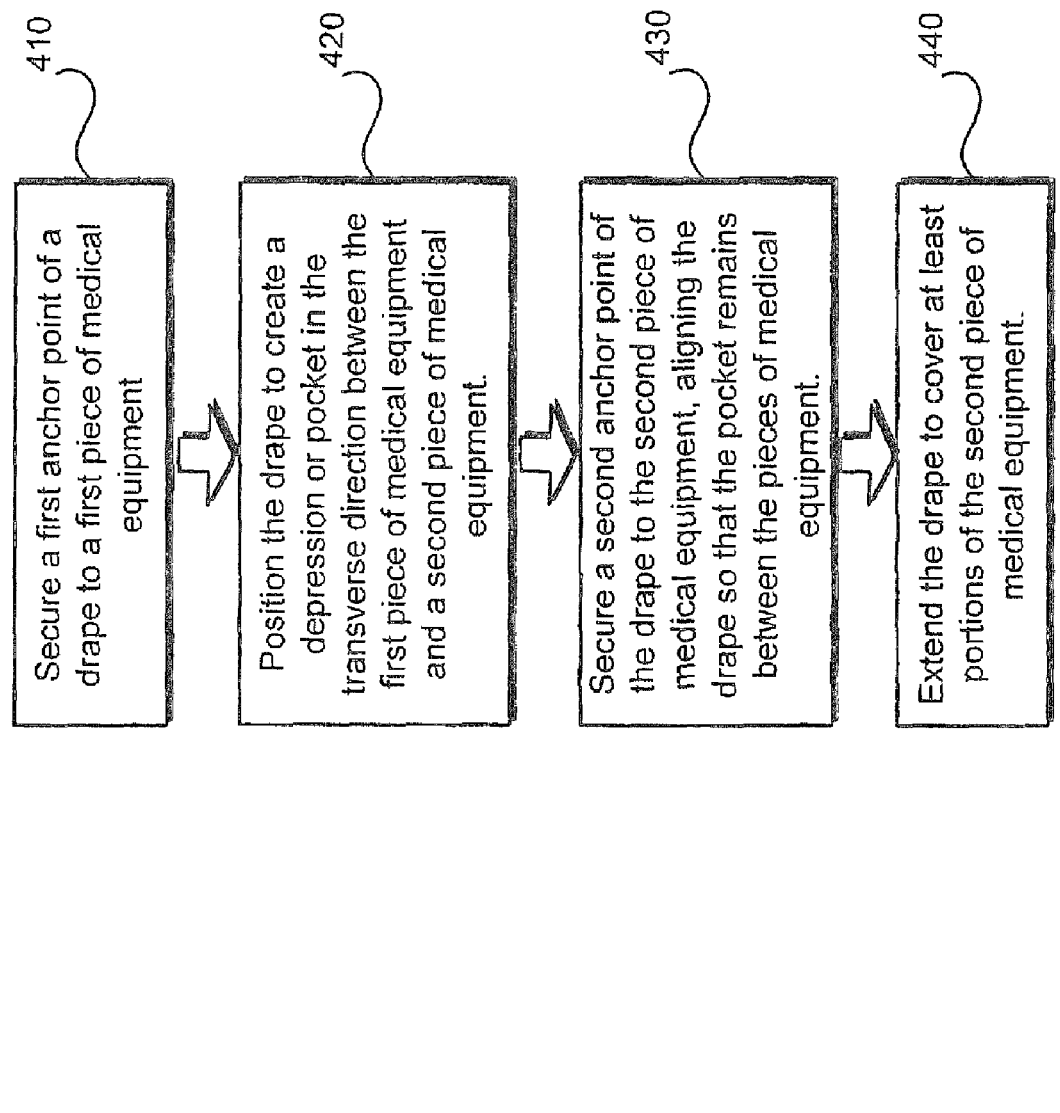
FIG. 4 illustrates exemplary operations for draping medical equipment.

FIG. 4 illustrates exemplary operations 400 for draping medical equipment. In operation 410, a first anchor point of a drape is secured to a first piece of medical equipment. In an implementation, the drape may be anchored to the first piece of medical equipment using one or more of a hook and loop fastener, snap, ribbon, button, tie, drawstring, adhesive, hook and eye fastener, vinyl adhering fastener, sticky glue, tab, hooking device, slot, belt interlocking device, or any other fastening mechanism or device. In operation 420, a medical professional or other user positions the drape to create a depression or pocket between the first piece of medical equipment and a second piece of medical equipment. In an implementation, this pocket may be formed in the transverse direction. In another implementation, this pocket may be formed by pleating in the drape, and the drape is positioned such that the pleating is located between the first and second pieces of medical equipment. In operation 430, a second anchor point of the drape is secured to the second piece of medical equipment, such that the pocket created between the first and second pieces of medical equipment remains. In operation 440, the drape is extended to cover at least portions of the second piece of medical equipment. However, it should be understood that coverage of the second piece of medical equipment is not required.

In one implementation, the second piece of medical equipment is a paddle used for compression of the breast during an imaging or biopsy procedure. The drape may be fed through a portion of the paddle to partially cover the paddle. Further, the drape may be extended to cover additional pieces of medical equipment. It should be understood that additional pockets may be formed in the drape by securing the drape to additional pieces of equipment or other underlying structures so that a depression is created in the drape.

The above specification and examples provide a complete description of the structure and use of example implementations of the invention. Although various implementations of the invention have been described above with a certain degree of particularity, or with reference to one or more individual embodiments, those skilled in the art could make numerous alterations to the disclosed embodiments without departing from the spirit or scope of this invention. Other implementations are therefore contemplated. It is intended that all matter contained in the above description and shown in the accompanying drawings shall be interpreted as illustrative only of particular implementations and not limiting. Changes in detail or structure may be made without departing from the basic elements of the invention as defined in the following claims.

Although the subject matter has been described in language specific to structural features and/or methodological arts, it is to be understood that the subject matter defined in the appended claims is not necessarily limited to the specific features or acts descried above. Rather, the specific features and acts described above are disclosed as example forms of implementing the claimed subject matter.

What is claimed is:

1. A draping system comprising:
    a drape portion having a long axis and a transverse axis, wherein the drape portion forms a pocket configured to collect debris extending lengthwise along the transverse axis of the drape portion;
    a first anchor portion in the drape portion positioned on one side of the pocket along the long axis of the drape portion, the first anchor portion adapted to secure the drape portion to a first medical equipment component; and
    a second anchor portion in the drape portion positioned on the other side of the pocket along the long axis of the drape portion, the second anchor portion adapted to secure the drape portion to a second medical equipment component, wherein the pocket is configured to lie between the first and second anchor portions.

2. The draping system of claim 1, wherein the pocket is formed by creating one or more folds in the drape portion and securing edges of the drape portion adjacent the folds together.

3. The draping system of claim 1, wherein the first medical equipment component includes a biopsy system and the pocket is configured to hang below the first anchor portion and the second anchor portion when the draping system is secured to the biopsy system.

4. The draping system of claim 1, wherein the first medical equipment component includes a biopsy system and the drape portion is configured to pass through a paddle component of the biopsy system, secure to a paddle component of the biopsy system, or pass through and secure to a paddle component of the biopsy system.

5. The draping system of claim 1, wherein the first anchor portion is separable from the second anchor portion.

6. The draping system of claim 1, wherein the drape portion further comprises one or more apertures, each aperture at least partially surrounded by a nonporous elastic membrane.

7. The draping system of claim 6, wherein the apertures are slits in the nonporous elastic membrane and at least a portion of the first medical equipment component or the second medical equipment component is configured to pass through one or more of the slits.

8. The draping system of claim 7, wherein two edges of each slit are configured to be fastened together to form a seal around the portion of the first medical equipment component or the second medical equipment component configured to pass through the one or more of the slits.

9. The draping system of claim 1, wherein the drape portion has one or more perforated slits about the transverse axis of the drape portion, wherein the drape portion is configured to be divided along the perforated slits.

10. The draping system of claim 1, wherein the first anchor portion is further adapted to extend through the first medical equipment component.

11. The draping system of claim 1, wherein the drape portion is a single continuous sheet of material.

12. The draping system of claim 1, wherein the first anchor portion and the second anchor portion are continuous with the pocket.

13. The draping system of claim 1, wherein the first anchor portion is continuous with the one side of the pocket and the second anchor portion is continuous with the other side of the pocket.

14. A draping system comprising:
    a drape portion having a long axis and a transverse axis, wherein the drape portion forms a pocket configured to collect debris extending lengthwise along the transverse axis of the drape portion;
    a first anchor portion in the drape portion positioned on one side of the pocket along the long axis of the drape portion, the first anchor portion configured to form a slit at least partially surrounded by a nonporous elastic membrane, wherein two edges of the slit are configured to be fastened together to form a seal around a first medical equipment component protruding through the slit; and
    a second anchor portion in the drape portion positioned on the other side of the pocket along the long axis of the drape portion, the second anchor portion adapted to secure the drape portion to a second medical equipment component.

15. The draping system of claim 14, wherein the pocket is formed by creating one or more folds in the drape portion and securing edges of the folds together.

16. The draping system of claim 14, wherein the first medical equipment component include a biopsy system and the pocket is configured to hang below the first anchor portion and the second anchor portion when the draping system is secured to the biopsy system.

17. The draping system of claim 14, wherein the first medical equipment component includes a biopsy system and the drape portion is configured to pass through a paddle component of the biopsy system, secure to a paddle component of the biopsy system, or pass through and secure to a paddle component of the biopsy system.

18. The draping system of claim 17, wherein the drape portion comprises one or more perforations in the transverse direction in the area of the drape portion that is configured to pass through the paddle component of the biopsy system.

19. The draping system of claim 14, wherein the nonporous elastic membrane forms a collar around the first medical equipment component.

20. A draping system comprising:
    a drape portion having a long axis and a transverse axis, wherein the drape portion forms a first pocket configured to collect debris extending lengthwise along the transverse axis of the drape portion;
    a first anchor portion in the drape portion positioned on one side of the pocket along the long axis of the drape portion, the first anchor portion configured to form a slit at least partially surrounded by a nonporous elastic membrane; and a second anchor portion in the drape portion positioned on the other side of the pocket along the long axis of the drape portion, the second anchor portion adapted to secure the drape portion to medical equipment, wherein the first anchor portion is separable from the second anchor portion and the first and second anchor portions are each configured to attach to opposing sides of a paddle component of the medical equipment.

21. The draping system of claim 20, wherein the pocket is formed by creating one or more folds in the drape portion and securing edges of the folds together.

22. The draping system of claim 20, wherein the pocket is configured to hang below the first anchor portion and the second anchor portion when the draping system is secured to the medical equipment.

23. The draping system of claim 20, wherein the drape portion further forms a second pocket positioned on the opposite side of the first anchor portion from the first pocket, wherein the second pocket is configured to collect debris and extends lengthwise along the transverse axis of the drape portion, and the second pocket is surrounded by a ridge to prevent leakage.

24. The draping system of claim 20, wherein the drape portion is configured to cover the medical equipment, the medical equipment includes biopsy equipment, and a support for a needle guide is accepted by the aperture at least partially surrounded by the nonporous elastic membrane.

25. The draping system of claim 20, wherein the nonporous elastic membrane stretches to accommodate movement of the needle guide.

26. The draping system of claim 20, wherein the drape portion, the first anchor portion, and the second anchor portion each include an absorbent material.

27. The draping system of claim 20, wherein the first anchor portion is separable from the second anchor portion along one or more perforated slits about the transverse axis of the drape portion.

28. A method for draping medical equipment with a drape having a long axis and a transverse axis and first and second anchor portions, comprising:

inserting a first piece of medical equipment through an aperture in the first anchor portion of the drape, wherein the aperture is at least partially surrounded by a nonporous elastic material;

positioning a pocket configured to collect debris extending lengthwise along the transverse axis of the drape between the first piece of medical equipment and a second piece of medical equipment; and securing the second anchor portion of the drape to the second piece of medical equipment such that the pocket remains between the first and second pieces of medical equipment.

29. The method of claim 28, further comprising:

separating the first anchor portion from the second anchor portion along one or more perforated slits about the transverse axis of the drape.

\* \* \* \* \*